(12) United States Patent
Tang et al.

(10) Patent No.: US 10,040,771 B2
(45) Date of Patent: Aug. 7, 2018

(54) METHOD FOR PREPARING PROSTACYCLIN RECEPTOR AGONIST 4-[N-(5,6-DIPHENYLPYRAZIN-2-YL)-N-ISOPROPYLAMINO]-1-BUTANOL

(71) Applicant: SEASONS BIOTECHNOLOGY (TAIZHOU) CO., LTD., Taizhou (CN)

(72) Inventors: Fanghui Tang, Shanghai (CN); Chi Ma, Shanghai (CN); Qiang Jia, Shanghai (CN)

(73) Assignee: SEASONS BIOTECHNOLOGY (TAIZHOU) CO., LTD., Taizhou (CN)

( * ) Notice: Subject to any disclaimer, the term of this patent is extended or adjusted under 35 U.S.C. 154(b) by 0 days.

(21) Appl. No.: 15/552,764

(22) PCT Filed: Mar. 31, 2016

(86) PCT No.: PCT/CN2016/000179
§ 371 (c)(1),
(2) Date: Aug. 22, 2017

(87) PCT Pub. No.: WO2016/180033
PCT Pub. Date: Nov. 17, 2016

(65) Prior Publication Data
US 2018/0029998 A1    Feb. 1, 2018

(30) Foreign Application Priority Data
May 13, 2015   (CN) .......................... 2015 1 0253314

(51) Int. Cl.
*C07D 241/20*   (2006.01)
(52) U.S. Cl.
CPC ................................. *C07D 241/20* (2013.01)

(58) Field of Classification Search
USPC ........................................................ 544/336
See application file for complete search history.

(56) References Cited

FOREIGN PATENT DOCUMENTS

| CN | 102459198 B | 6/2012 |
|----|-------------|--------|
| WO | 2002088084 A1 | 7/2002 |
| WO | 2011017612 A1 | 10/2011 |

OTHER PUBLICATIONS

Asaki, T. et al., "Structure-activity studies on diphenylpyrazine derivatives: a novel class of prostacyclin receptor agonists," Bioorganic & Medicinal Chemistry, vol. 15, No. 21, Aug. 15, 2007, pp. 6692-6704.
International Search Report and Written Opinion from PCT/CN2016/000180 dated Jul. 7, 2016.
International Search Report for International Application No. PCT/CN2016/000179 dated Jul. 7, 2016.
Written Opinion for International Application No. PCT/CN2016/000179 dated Jul. 7, 2016.
International Preliminary Report on Patentability for International Application No. PCT/CN2016/000179 dated Nov. 14, 2017.

*Primary Examiner* — Douglas M Willis
(74) *Attorney, Agent, or Firm* — Zhaoyang Li

(57) ABSTRACT

The present invention relates to preparation methods of a prostacyclin receptor agonist of 2-{4-[N-(5,6-diphenylpyrazin-2-yl)-N-isopropylamino]butyloxy}-N-(methylsulfonyl)acetamide and its intermediates. These methods are simple and convenient to operate, environment-friendly and suitable for industrial production to obtain the product with good yield and high purity.

5 Claims, No Drawings

METHOD FOR PREPARING PROSTACYCLIN RECEPTOR AGONIST 4-[N-(5,6-DIPHENYLPYRAZIN-2-YL)-N-ISOPROPYLAMINO]-1-BUTANOL

FIELD OF THE INVENTION

The present invention relates to the technical field of chemical synthesis in pharmaceutical industry. Specifically, it relates to preparation methods of a prostacyclin receptor agonist of 2-{4-[N-(5,6-diphenylpyrazin-2-yl)-N-isopropylamino]butyloxy}-N-(methyl sulfonyl)acetamide.

BACKGROUND OF THE INVENTION

Selexipag is known chemically as 2-{4-[N-(5,6-diphenylpyrazin-2-yl)-N-isopropylamino]butyloxy}-N-(methylsulfonyl)acetamide, also named ACT-293987 or NS-304 (for convenience, it is also referred to NS-304 in the present invention.). Its structural formula is shown below:

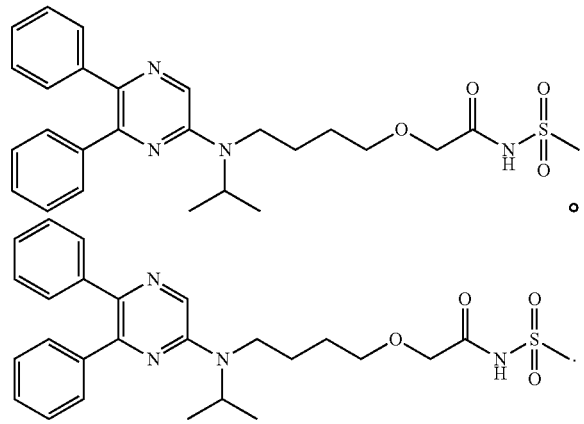

NS-304 was invented by Nippon Shinyaku Co. Ltd., which had good prostacyclin (PGI2) receptor agonist activity and effects of inhibiting platelet aggregation, dilation of blood vessels, dilation of bronchial muscle, inhibiting lipid deposition and inhibiting leukocyte activation. Actelion Pharmaceuticals Co. Ltd. has submitted the new drug application of NS-304 as a pulmonary arterial hypertension (PAH) drug to U.S. FDA. Phase III clinical data showed that this oral drug could reduce the morbidity/mortality of pulmonary arterial hypertension patients by 39% compared with placebo.

Patent Document WO2002088084A1 first reported a preparation method of NS-304, which comprising the following steps: (1) reacting 2-chloro-5,6-diphenylpyrazine with 4-isopropylamino-1-butanol to obtain 4-[N-(5,6-diphenylpyrazine-2-yl)-N-isopropylamino]-1-butanol; (2) reacting 4-[N-(5,6-diphenylpyrazine-2-yl)-N-isopropylamino]-1-butanol with tert-butyl bromoacetate to obtain 2-{4-[N-(5,6-diphenylpyrazine-2-yl)-N-isopropylamino]butyloxy}acetic acid tert-butyl ester; (3) hydrolyzing 2-{4-[N-(5,6-diphenylpyrazine-2-yl)-N-isopropylamino]butyloxy}acetic acid tert-butyl ester to obtain 2-{4-[N-(5,6-diphenylpyrazine-2-yl)-N-isopropylamino]butyloxy}acetic acid; (4) reacting 2-{4-[N-(5,6-diphenylpyrazine-2-yl)-N-isopropylamino]butyloxy}acetic acid with 1,1-carbonyl diimidazole (CDI), then reacting with methanesulfonamide in the presence of 1,8-diazabicyclo[5.4.0]-7-undecene to obtaine NS-304. The reaction formula is shown below:

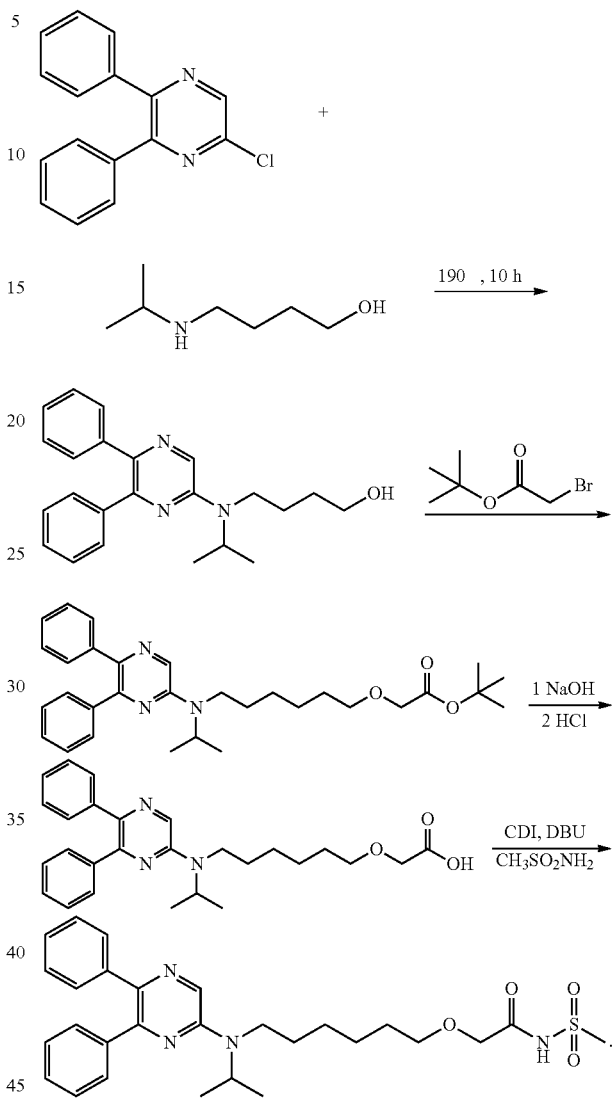

In this preparation method, 2-chloro-5,6-diphenylpyrazine was used as the raw material to obtain NS-304 by the multi-step reaction, the total yield was only 26%. Especially, in the step (1), the reaction selectivity was poor, purification was difficult and the molar yield was only 56%. The product of the step (1), 4-[N-(5,6-diphenylpyrazin-2-yl)-N-isopropylamino]-1-butanol, is an important intermediate in preparing of NS-304, its yield and purity can largely influence yield and purity of the final product which further may be difficult to achieve high quality requirements in pharmaceutical preparations. In addition, in steps (1), (2) and (4), silica gel column chromatography was needed in purification, which resulted in high cost, inefficiency, serious pollution and unsuitability for industrial production.

Patent Document CN102459198A reported another preparation method of NS-304, which comprising the following steps: (1) reacting 2-chloro-5,6-diphenylpyrazine with sodium iodide to obtain 2-iodo-5,6-diphenylpyrazine; (2) in the presence of an alkali, reacting 2-iodo-5,6-diphenylpyrazine with 4-isopropylamino-1-butanol in an organic solvent at 170-200° C. for 5-9 hours to obtain 4-[N-(5,6-diphenylpyrazine-2-yl)-N-isopropylamino]-1-butanol, wherein the organic solvent was, for example, sulfolane, N-methylpyrrolidone, N,N-dimethyl imidazolidinone, dimethyl sulfoxide or a mixed solvent thereof; (3) reacting 4-[N-(5,6-diphenylpyrazine-2-yl)-N-isopropylamino]-1-butanol with N-(chloroacetyl)methanesulfonamide to obtain NS-304. The reaction formula is shown below:

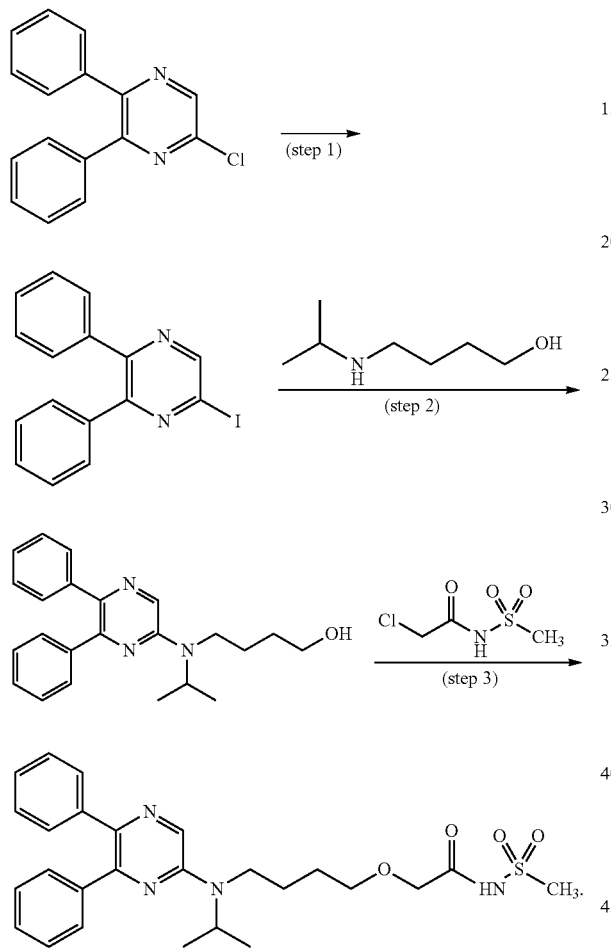

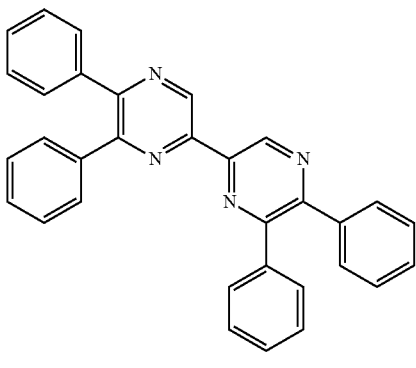

impurity S

SUMMARY OF THE INVENTION

In view of the defects in the conventional methods, the objective of the present invention is to provide novel preparation methods of NS-304, also preparation methods of its intermediates. These preparation methods are simple and convenient to operate, environment-friendly and suitable for industrial production to obtain the product with good yield and high purity.

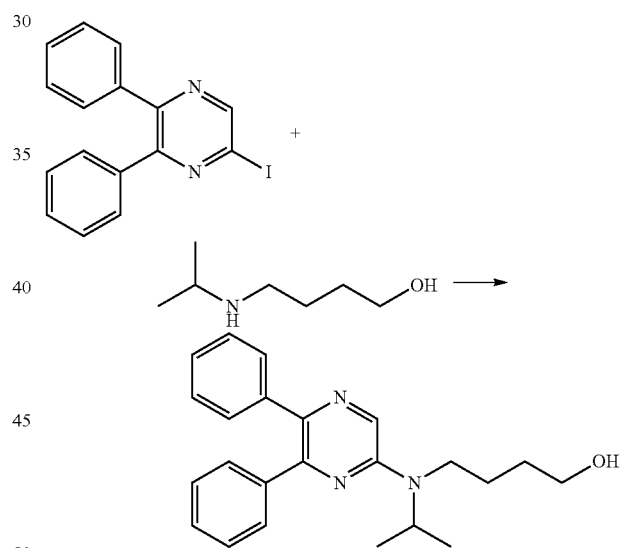

According to the objective of the present invention, a preparation method of the NS-304 intermediate of 4-[N-(5,6-diphenylpyrazin-2-yl)-N-isopropylamino]-1-butanol is provided, which comprising: reacting 2-iodo-5,6-diphenylpyrazin with 4-isopropylamino-1-butanol to obtain 4-[N-(5,6-diphenylpyrazin-2-yl)-N-isopropylamino]-1-butanol, wherein the reaction is carried out in the absence of solvents and acid-binding agents.

The acid-binding agents are known to those skilled in the art and usually refer to reagents which can combine with small molecular acidic substances generated in the reaction and promote the positive reaction. Commonly used acid-binding agents are alkaline substances, such as carbonates, bicarbonates, phosphates, hydrogen phosphates, alkali metal hydroxides, alkaline earth metal hydroxides or mixtures thereof, or organic amines, specific examples are sodium CN102459198A did not provide specific preparation examples, but the present inventors found some defects in this preparation method by studies. Strong polar organic solvents with high boiling points were used in the step (2), they were unstable during the long time reaction at high temperature of 170-200° C. and led to side reactions, post-treatment and separating of solvents and the product were difficult, a lot of water was needed to quench the reaction and waste water was difficult to handle; when placed in a high-temperature alkaline environment, the condensation reaction of 2-iodo-5,6-diphenylpyrazine may occur and produce lots of impurity S (its structural formula is shown below); in the step (2), the reaction had poor selectivity, low yield and high cost, column chromatography was needed in the separation process of post-treatment, it was unsuitable for industrial production. In addition, in the step (3), removing excessive N-(chloroacetyl)methanesulfonamide and purification of the product were difficult.

carbonate, potassium carbonate, sodium bicarbonate, potassium bicarbonate, sodium phosphate, potassium phosphate, sodium hydrogen phosphate, potassium hydrogen phosphate, sodium hydroxide, potassium hydroxide, calcium hydroxide, triethylamine, pyridine, diisopropylethylamine or isopropylamine.

Preferably, the molar ratio of 4-isopropylamino-1-butanol to 2-iodo-5,6-diphenylpyrazin is 1:1 to 20:1; more preferably, the molar ratio of 4-isopropylamino-1-butanol to 2-iodo-5,6-diphenylpyrazin is 5:1 to 15:1.

The reaction temperature of the above reaction is 130 to 200° C. and the reaction time is 2 to 10 hours; preferably, the reaction temperature is 150 to 180° C. and the reaction time is 3 to 6 hours.

After completion of the reaction, 4-isopropylamino-1-butanol is recovered by vacuum distillation, and HPLC purity of 4-[N-(5,6-diphenylpyrazin-2-yl)-N-isopropylamino]-1-butanol is up to 96.0%. Further, the product can be purified by recrystallization, so its HPLC purity will up to 99.0% and the molar yield will over 85%.

Compared with conventional methods, the preparation method of 4-[N-(5,6-diphenylpyrazin-2-yl)-N-isopropylamino]-1-butanol in the present invention has significant advantages: since solvents and acid-binding agents are not used, the reaction selectivity is good, post-treatment is simple, complicated purifications in the conventional methods, such as silica gel column chromatography, are not required; free of impurity S, the product has good yield and high purity, waste pollution is less, and it is suitable for process scale and industrial production. Especially, 4-[N-(5,6-diphenylpyrazin-2-yl)-N-isopropylamino]-1-butanol with good yield and high purity prepared by the present method is suitable for being used as an intermediate in the preparation of NS-304.

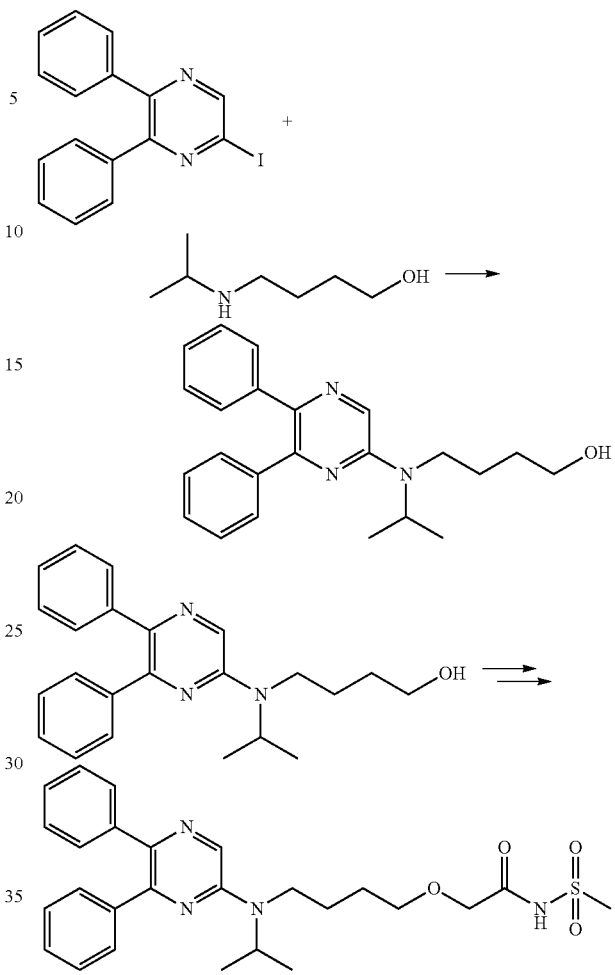

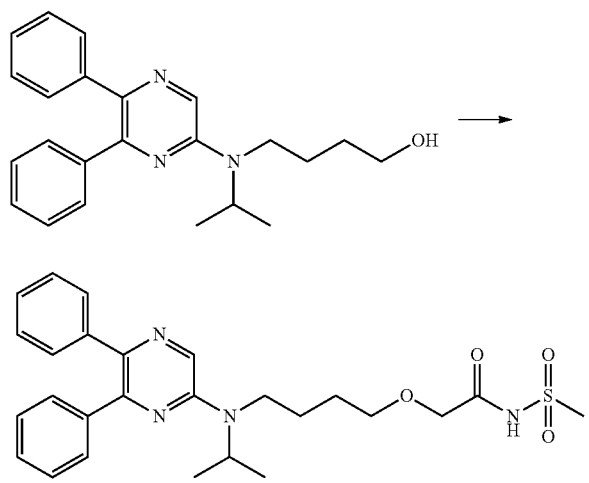

According to the objective of the present invention, a preparation method of 2-{4-[N-(5,6-diphenylpyrazin-2-yl)-N-isopropylamino]butyloxy}-N-(methylsulfonyl)acetamide is provided, which comprising: using 4-[N-(5,6-diphenylpyrazin-2-yl)-N-isopropylamino]-1-butanol obtained according to above preparation methods in the present invention to prepare 2-{4-[N-(5,6-diphenylpyrazin-2-yl)-N-isopropylamino]butyloxy}-N-(methylsulfonyl)acetamide.

Further, the preparation method of 2-{4-[N-(5,6-diphenylpyrazin-2-yl)-N-isopropylamino]butyloxy}-N-(methylsulfonyl)acetamide provided in the present invention comprises the following steps:

(1) in the absence of solvents and acid-binding agents, reacting 2-iodo-5,6-diphenylpyrazin with 4-isopropylamino-1-butanol to obtain 4-[N-(5,6-diphenylpyrazin-2-yl)-N-isopropylamino]-1-butanol, wherein the molar ratio of 4-isopropylamino-1-butanol to 2-iodo-5,6-diphenylpyrazin is 1:1 to 20:1, the reaction temperature is 130 to 200° C., the reaction time is 2 to 10 hours, and 4-isopropylamino-1-butanol is recovered by vacuum distillation after completion of the reaction;

(2) using 4-[N-(5,6-diphenylpyrazin-2-yl)-N-isopropylamino]-1-butanol obtained in the step (1) to prepare 2-{4-[N-(5,6-diphenylpyrazin-2-yl)-N-isopropylamino]butyloxy}-N-(methyl sulfonyl)acetamide.

Definitions and examples of the above acid-binding agents are same as the previous descriptions in the present specification.

Preferably, in the above step (1), the molar ratio of 4-isopropylamino-1-butanol to 2-iodo-5,6-diphenylpyrazin is 5:1 to 15:1, the reaction temperature is 150 to 180° C., and the reaction time is 3 to 6 hours.

Preferably, the above step (2) includes the following steps (2a) to (2c):

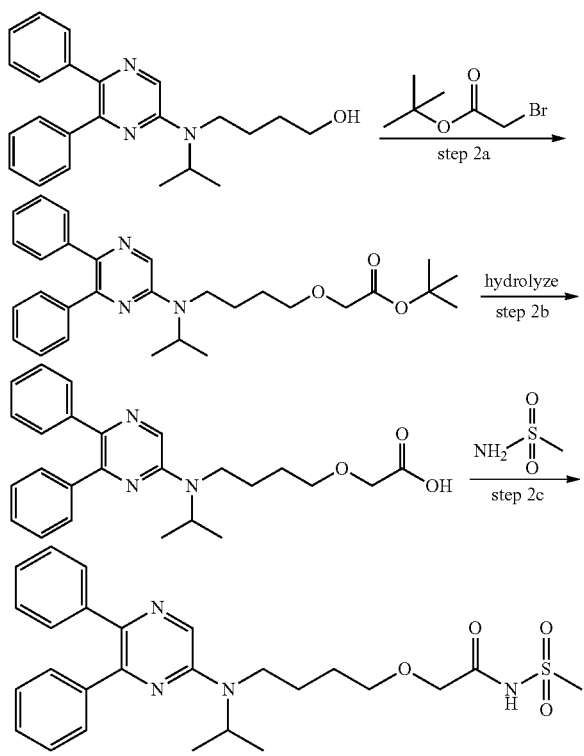

(2a) in the presence of a phase transfer catalyst, reacting 4-[N-(5,6-diphenylpyrazin-2-yl)-N-isopropylamino]-1-butanol obtained in the step (1) with tert-butyl bromoacetate in an organic solvent and an aqueous solution of alkali metal hydroxide to obtain 2-{4-[N-(5,6-diphenylpyrazin-2-yl)-N-isopropylamino]butyloxy}tert-butyl acetate, wherein the molar ratio of 4-[N-(5,6-diphenylpyrazin-2-yl)-N-isopropylamino]-1-butanol to tert-butyl bromoacetate is 1:1 to 1:5, the organic solvent is selected from the group consisting of halogenated alkanes and aromatic alkanes, the alkali metal hydroxide is selected from the group consisting of sodium hydroxide, potassium hydroxide, lithium hydroxide and the mixtures thereof, and the phase transfer catalyst is selected from the group consisting of tetrabutylammonium bromide, tetrabutylammonium hydrogen sulfate and cetyltrimethylammonium bromide;

(2b) hydrolyzing 2-{4-[N-(5,6-diphenylpyrazin-2-yl)-N-isopropylamino]butyloxy}tert-butyl acetate to obtain 2-{4-[N-(5,6-diphenylpyrazin-2-yl)-N-isopropylamino]butyloxy} acetic acid;

(2c) in the presence of a chlorinating agent and an acid-binding agent, reacting 2-{4-[N-(5,6-diphenylpyrazin-2-yl)-N-isopropylamino]butyloxy}acetic acid with methanesulfonamide to obtain 2-{4-[N-(5,6-diphenylpyrazin-2-yl)-N-isopropylamino]butyloxy}-N-(methylsulfonyl) acetamide.

In the step (2a): the organic solvent is preferably dichloromethane or toluene. The molar amount of the alkali metal hydroxide is 10 to 50 times of that of 4-[N-(5,6-diphenylpyrazin-2-yl)-N-isopropylamino]-1-butanol. The reaction temperature is preferably 0 to 50° C. After completion of the reaction, without using silica gel column chromatography for purification, the product is separated by conventional treatment methods, such as extraction or removing the solvent by concentration, to obtain NS-304 with high purity.

The hydrolyzing reaction in the step (2b) is known to those skilled in the art. Preferably, the hydrolyzing reaction is carried out under alkaline conditions. Specific operations such as: reacting 2-{4-[N-(5,6-diphenylpyrazin-2-yl)-N-isopropylamino]butyloxy}tert-butyl acetate with an alkali metal hydroxide in the mixture solution of alcohol and water, then obtaining 2-{4-[N-(5,6-diphenylpyrazin-2-yl)-N-isopropylamino]butyloxy} acetic acid by acidification. The molar ratio of 2-{4-[N-(5,6-diphenylpyrazin-2-yl)-N-isopropylamino]butyloxy}tert-butyl acetate to the alkali metal hydroxide is 1:1.1 to 1:5.0. The alkali metal hydroxide is selected from the group consisting of sodium hydroxide, potassium hydroxide and lithium hydroxide. After completion of the reaction, excess alkali is neutralized by adding an acid, the acid such as hydrochloric acid, sulfuric acid or acetic acid.

In the step (2c), 2-{4-[N-(5,6-diphenylpyrazin-2-yl)-N-isopropylamino]butyloxy}acetic acid firstly reacts with a chlorinating agent to obtain an active acyl chloride intermediate, then the unseparated intermediate directly reacts with methanesulfonamide to obtain 2-{4-[N-(5,6-diphenylpyrazin-2-yl)-N-isopropylamino]butyloxy}-N-(methylsulfonyl)acetamide. Preferably, the chlorinating agent is selected from the group consisting of phosphorus oxychloride, thionyl chloride, triphosgene and oxalyl chloride. The molar ratio of 2-{4-[N-(5,6-diphenylpyrazin-2-yl)-N-isopropylamino]butyloxy} acetic acid to the chlorinating agent is 1:1 to 1:2, and the molar ratio of 2-{4-[N-(5,6-diphenylpyrazin-2-yl)-N-isopropylamino]butyloxy}acetic acid to methanesulfonamide is 1:1 to 1:3. The solvent of the reaction is selected from the group consisting of halogenated alkanes, ethers, aromatic alkanes and acetonitrile, preferably, dichloromethane, tetrahydrofuran or acetonitrile. After completion of the reaction, the product is separated and purified by conventional treatment methods, such as extraction or removing the solvent by concentration. Without using silica gel column chromatography for purification, the crude product can be directly purified by recrystallization to obtain NS-304 with high purity.

Definitions and examples of the acid-binding agents in the step (2c) are same as the previous descriptions in the present specification.

EXAMPLES

The following examples will further help to understand the present invention, but not be used to restrict the scope of the present invention.

The reagents used in the examples are purchased commercially.

In the examples, room temperature refers to 10° C. to 30° C.

The test instruments and methods in the examples:

AV-400 proton nuclear magnetic resonance spectroscopy (Bruker Corporation, Germany);

LC-20AT high performance liquid chromatography (Shimadzu Corporation, Japan);

HPLC test conditions: Phenomenon luna chromatography column C18, 5 μm, 4.6 mm×250 mm; detection wavelength (UV) is 290 nm; running time is 15 minutes; mobile phase is acetonitrile:water (0.05% trifluoroacetate)=85%:15%.

Example 1

(1) Preparation of 4-[N-(5,6-diphenylpyrazin-2-yl)-N-isopropylamino]-1-butanol 35.8 g (0.1 mol) of 2-iodo-5,6-diphenylpyrazin and 104 g (0.8 mol) of 4-isopropylamino-1-butanol were added into a 500 mL flask. Under the protection of nitrogen, the mixture was heated to 150° C. and reacted at this temperature for 10 hours, then cooled to 120° C. 80 g of 4-isopropylamino-1-butanol was recovered by vacuum distillation, the residue was cooled and samples were taken for testing, HPLC purity of the product was 95.3%. 300 mL of 95% aqueous ethanol was added to recrystallize, and 30.7 g white solids of 4-[N-(5,6-diphenylpyrazin-2-yl)-N-isopropylamino]-1-butanol was obtained, the molar yield was 85%, HPLC purity was 99.3%, free of impurity S.

$^1$H-NMR data: $^1$H-NMR (400 MHz, CDCl$_3$) δ 8.02 (s, 1H), 7.46 (d, 2H, J=7.6 Hz), 7.36 (d, 2H, J=7.2 Hz), 7.28-7.22 (m, 6H), 4.80-4.78 (m, 1H), 3.71 (t, 2H, J=6.4 Hz), 3.45 (t, 2H, J=7.6 Hz), 1.77-1.74 (m, 2H), 1.66-1.64 (m, 2H), 1.29 (d, 6H, J=6.8 Hz).

(2) Preparation of 2-{4-[N-(5,6-diphenylpyrazin-2-yl)-N-isopropylamino] butyloxy}tert-butyl acetate 18.5 g (0.05 mol) of 4-[N-(5,6-diphenylpyrazin-2-yl)-N-isopropylamino]-1-butanol, 200 mL of dichloromethane, 40 g of 45% aqueous solution of sodium hydroxide and 2 g of tetrabutylammonium bromide were added into a 500 mL flask and cooled to 5° C. by ice water, 19.5 g (0.1 mol) of tert-butyl bromoacetate was added dropwise, then the mixture reacted at this temperature for 2 hours until HPLC analysis showed the raw materials were reacted completely.

The mixture was placed to separate into layers, the aqueous phase was extracted once with 100 mL of dichloromethane, the combined organic phase was washed with water and dried with anhydrous sodium sulfate, concentrated, dichloromethane was recovered, and 23 g of 2-{4-[N-(5,6-diphenylpyrazin-2-yl)-N-isopropylamino] butyloxy}tert-butyl acetate was obtained, the molar yield was 97%, HPLC purity was 95%.

(3) Preparation of 2-{4-[N-(5,6-diphenylpyrazin-2-yl)-N-isopropylamino] butyloxy} acetic acid 23 g of 2-{4-[N-(5,6-diphenylpyrazin-2-yl)-N-isopropylamino]butyloxy}tert-butyl acetate (obtained by the previous reaction) and 115 mL of methanol were added into a 500 mL flask and cooled to 0° C., 8 g of 50% aqueous solution of sodium hydroxide was added dropwise, then reacted at this temperature for 2 hours until the reaction was completed.

The reaction solution was adjusted to pH 1-2 with 2N hydrochloric acid, then extracted by ethyl acetate, the organic phase was concentrated, the obtained crude product was recrystallized by 100 mL of isopropanol, and 17.4 g of 2-{4-[N-(5,6-diphenylpyrazin-2-yl)-N-isopropylamino] butyloxy} acetic acid was obtained, the molar yield was 83%, HPLC purity was 98.9%.

$^1$H-NMR data: $^1$H-NMR (400 MHz, CDCl$_3$) δ 8.03 (s, 1H), 7.35 (d, 2H, J=7.2 Hz), 7.24 (d, 2H, J=7.2 Hz), 7.17-7.15 (m, 6H), 4.80-4.77 (m, 1H), 4.0 (s, 2H), 3.56 (t, 2H, J=6.0 Hz), 3.38 (t, 2H, J=6.4 Hz), 1.71-1.66 (m, 4H), 1.20 (d, 6H, J=6.8 Hz).

(4) Preparation of NS-304

8.4 g (0.02 mol) of 2-{4-[N-(5,6-diphenylpyrazin-2-yl)-N-isopropylamino] butyloxy} acetic acid and 60 mL of acetonitrile were added into a 100 mL flask and cooled to 5° C., 3.8 g (0.03 mol) of oxalyl chloride was added dropwise, then reacted at room temperature for 2 hours, the solvent was concentrated to dryness, 50 mL of acetonitrile was added to dissolve, and the ×1 solution was obtained as a stand-by.

2.85 g of methanesulfonamide, 20 mL of acetonitrile and 3 g of triethylamine were added into another flask and cooled to 10° C., the ×1 solution obtained above was added dropwise, then reacted at this temperature for 5 hours until the reaction was completed.

The finished reaction solution was poured into 100 mL of ice water, the mixture was extracted with ethyl acetate, the solvent of the organic phase was concentrated to dryness, the residue was recrystallized with ethanol, and 8.5 g off-white crystals of NS-304 was obtained, the molar yield was 86%, HPLC purity was 99.5%.

$^1$H-NMR data: $^1$H-NMR (400 MHz, CDCl$_3$) δ: 8.19 (s, 1H), 7.44 (m, 2H), 7.35 (m, 2H), 7.30-7.21 (m, 6H), 3.97 (s, 2H), 3.59 (t, J=6.0 Hz, 2H), 3.45 (t, J=6.8 Hz, 2H), 3.29 (s, 3H), 1.75-1.70 (m, 4H).

Example 2

(1) Preparation of 4-[N-(5,6-diphenylpyrazin-2-yl)-N-isopropylamino]-1-butanol 35.8 g (0.1 mol) of 2-iodo-5,6-diphenylpyrazin and 197 g (1.5 mol) of 4-isopropylamino-1-butanol was added into a 500 mL flask. Under the protection of nitrogen, the mixture was heated to 180° C. and reacted at this temperature for 2 hours, then cooled to 120° C. 150 g of 4-isopropylamino-1-butanol was recovered by vacuum distillation, the residue was cooled and samples were taken for testing, HPLC purity of the product was 96.2%, acetonitrile was added to recrystallize, and 29.2 g white solids of 4-[N-(5,6-diphenylpyrazin-2-yl)-N-isopropylamino]-1-butanol was obtained, the molar yield was 81%, HPLC purity was 99.2%, free of impurity S.

$^1$H-NMR data: $^1$H-NMR (400 MHz, CDCl$_3$) δ 8.02 (s, 1H), 7.46 (d, 2H, J=7.6 Hz), 7.36 (d, 2H, J=7.2 Hz), 7.28-7.22 (m, 6H), 4.80-4.78 (m, 1H), 3.71 (t, 2H, J=6.4 Hz), 3.45 (t, 2H, J=7.6 Hz), 1.77-1.74 (m, 2H), 1.66-1.64 (m, 2H), 1.29 (d, 6H, J=6.8 Hz).

(2) Preparation of 2-{4-[N-(5,6-diphenylpyrazin-2-yl)-N-isopropylamino] butyloxy}tert-butyl acetate 18.5 g (0.05 mol) of 4-[N-(5,6-diphenylpyrazin-2-yl)-N-isopropylamino]-1-butanol, 200 mL of toluene, 40 g of 45% aqueous solution of potassium hydroxide and 2 g of tetrabutylammonium bromide were added into a 500 mL flask and cooled to 5° C. by ice water, 50 g (0.25 mol) of tert-butyl bromoacetate was added dropwise, then reacted at this temperature for 2 hours until HPLC analysis showed the raw materials were reacted completely.

The mixture was placed to separate into layers, the aqueous phase was extracted once with 100 mL of toluene, the combined organic phase was washed with water and dried with anhydrous sodium sulfate, concentrated, toluene was recovered, and 23.8 g of 2-{4-[N-(5,6-diphenylpyrazin-2-yl)-N-isopropylamino] butyloxy}tert-butyl acetate was obtained, the molar yield was 100%, HPLC purity was 94%.

(3) Preparation of 2-{4-[N-(5,6-diphenylpyrazin-2-yl)-N-isopropylamino] butyloxy} acetic acid 23.8 g of 2-{4-[N-(5,6-diphenylpyrazin-2-yl)-N-isopropylamino]butyloxy}tert-butyl acetate (obtained by the previous reaction) and 115 mL of anhydrous ethanol were added into a 500 mL flask and cooled to 0° C., 20 g of 50% aqueous solution of sodium hydroxide was added dropwise, then reacted at this temperature for 2 hours until the reaction was completed.

The reaction solution was adjusted to pH 1-2 with 2N sulfuric acid, then extracted with ethyl acetate, the organic phase was concentrated, the obtained crude product was recrystallized by 100 mL of isopropanol, and 16.7 g of 2-{4-[N-(5,6-diphenylpyrazin-2-yl)-N-isopropylamino] butyloxy} acetic acid was obtained, the molar yield was 80%, HPLC purity was 99.2%.

$^{1}$H-NMR data: $^{1}$H-NMR (400 MHz, CDCl$_3$) δ 8.03 (s, 1H), 7.35 (d, 2H, J=7.2 Hz), 7.24 (d, 2H, J=7.2 Hz), 7.17-7.15 (m, 6H), 4.80-4.77 (m, 1H), 4.0 (s, 2H), 3.56 (t, 2H, J=6.0 Hz), 3.38 (t, 2H, J=6.4 Hz), 1.71-1.66 (m, 4H), 1.20 (d, 6H, J=6.8 Hz).

(4) Preparation of NS-304

8.4 g (0.02 mol) of 2-{4-[N-(5,6-diphenylpyrazin-2-yl)-N-isopropylamino] butyloxy} acetic acid and 60 mL of acetonitrile were added into a 100 mL flask and cooled to 5° C., 6 g (0.04 mol) of phosphorus oxychloride was added dropwise, then kept the reflux reaction for 2 hours, and the ×2 solution was obtained as a stand-by.

2.85 g of methanesulfonamide, 20 mL of acetonitrile and 6 g of triethylamine were added into another flask and cooled to 10° C., the ×2 solution obtained above was added dropwise, then reacted at this temperature for 5 hours until the reaction was completed.

The finished reaction solution was poured into 100 mL of ice water, the mixture was extracted with ethyl acetate, the solvent of the organic phase was concentrated to dryness, the residue was recrystallized with ethanol, and 8.5 g off-white crystals of NS-304 was obtained, the molar yield was 86%, HPLC purity was 99.0%.

$^{1}$H-NMR data: $^{1}$H-NMR (400 MHz, CDCl$_3$) δ: 8.19 (s, 1H), 7.44 (m, 2H), 7.35 (m, 2H), 7.30-7.21 (m, 6H), 3.97 (s, 2H), 3.59 (t, J=6.0 Hz, 2H), 3.45 (t, J=6.8 Hz, 2H), 3.29 (s, 3H), 1.75-1.70 (m, 4H).

Example 3

(1) Preparation of 4-[N-(5,6-diphenylpyrazin-2-yl)-N-isopropylamino]-1-butanol 35.8 g (0.1 mol) of 2-iodo-5,6-diphenylpyrazin and 67 g (0.5 mol) of 4-isopropylamino-1-butanol was added into a 500 mL flask. Under the protection of nitrogen, the mixture was heated to 180° C. and reacted at this temperature for 10 hours, samples were taken for testing, HPLC purity of the product was 95.2%, then cooled to 20° C., 200 mL of ethyl acetate and 100 mL of water were added, stirred for 10 minutes and separated into layers, the solvent of ethyl acetate phase was concentrated to dryness, the residue was recrystallized with cyclohexane, and 27.4 g white solids of 4-[N-(5,6-diphenylpyrazin-2-yl)-N-isopropylamino]-1-butanol was obtained. The molar yield was 76% HPLC purity was 98.7% free of impurity S.

$^{1}$H-NMR data: $^{1}$H-NMR (400 MHz, CDCl$_3$) δ 8.02 (s, 1H), 7.46 (d, 2H, J=7.6 Hz), 7.36 (d, 2H, J=7.2 Hz), 7.28-7.22 (m, 6H), 4.80-4.78 (m, 1H), 3.71 (t, 2H, J=6.4 Hz), 3.45 (t, 2H, J=7.6 Hz), 1.77-1.74 (m, 2H), 1.66-1.64 (m, 2H), 1.29 (d, 6H, J=6.8 Hz).

(2) Preparation of 2-{4-[N-(5,6-diphenylpyrazin-2-yl)-N-isopropylamino]butyloxy}tert-butyl acetate 18.5 g (0.05 mol) of 4-[N-(5,6-diphenylpyrazin-2-yl)-N-isopropylamino]-1-butanol, 200 mL of toluene, 80 g of 45% aqueous solution of sodium hydroxide and 2 g of cetyltrimethylammonium bromide were added into a 500 mL flask and cooled by ice water to 5° C., 20 g (0.10 mol) of tert-butyl bromoacetate was added dropwise, then reacted at this temperature for 5 hours until HPLC analysis showed the raw materials were reacted completely.

The mixture was placed to separate into layers, the aqueous phase was extracted once with 100 mL of toluene, the combined organic phase was washed with water and dried with anhydrous sodium sulfate, concentrated, toluene was recovered, and 23.8 g of 2-{4-[N-(5,6-diphenylpyrazin-2-yl)-N-isopropylamino]butyloxy}tert-butyl acetate was obtained, the molar yield was 100%, HPLC purity was 96%.

(3) Preparation of 2-{4-[N-(5,6-diphenylpyrazin-2-yl)-N-isopropylamino] butyloxy} acetic acid 23.8 g of 2-{4-[N-(5,6-diphenylpyrazin-2-yl)-N-isopropylamino]butyloxy}tert-butyl acetate (obtained by the previous reaction) and 115 mL of anhydrous ethanol were added into a 500 mL flask and cooled to 0° C., 40 g of 30% aqueous solution of lithium hydroxide was added dropwise, then reacted at this temperature for 2 hours until the reaction was completed.

The reaction solution was adjusted to pH 1-2 with 2N sulfuric acid and extracted with ethyl acetate, the organic phase was concentrated, the obtained crude product was recrystallized by 100 mL of isopropanol, and 18.9 g of 2-{4-[N-(5,6-diphenylpyrazin-2-yl)-N-isopropylamino] butyloxy} acetic acid was obtained, the molar yield was 90%, HPLC purity was 99.2%.

$^{1}$H-NMR data: $^{1}$H-NMR (400 MHz, CDCl$_3$) δ 8.03 (s, 1H), 7.35 (d, 2H, J=7.2 Hz), 7.24 (d, 2H, J=7.2 Hz), 7.17-7.15 (m, 6H), 4.80-4.77 (m, 1H), 4.0 (s, 2H), 3.56 (t, 2H, J=6.0 Hz), 3.38 (t, 2H, J=6.4 Hz), 1.71-1.66 (m, 4H), 1.20 (d, 6H, J=6.8 Hz).

(4) Preparation of NS-304

8.4 g (0.02 mol) of 2-{4-[N-(5,6-diphenylpyrazin-2-yl)-N-isopropylamino] butyloxy} acetic acid, 60 mL of chloroform and 1 mL of DMF were added into a 100 mL flask and cooled to 5° C., 20 mL of chloroform solution containing 6 g (0.02 mol) of triphosgene was added dropwise, then kept the reflux reaction for 2 hours, and the ×3 solution was obtained as a stand-by.

2.85 g of methanesulfonamide, 20 mL of acetonitrile and 8 g of triethylamine were added into another flask and cooled to 10° C., the ×3 solution obtained above was added dropwise, then reacted at this temperature for 5 hours until the reaction was completed.

The finished reaction solution was poured into 100 mL of ice water, the mixture was extracted with ethyl acetate, the solvent of the organic phase was concentrated to dryness, the residue was recrystallized with ethanol, and 8.0 g off-white crystals of NS-304 was obtained, the molar yield was 80%, HPLC purity was 99.1%.

$^{1}$H-NMR data: $^{1}$H-NMR (400 MHz, CDCl$_3$) δ: 8.19 (s, 1H), 7.44 (m, 2H), 7.35 (m, 2H), 7.30-7.21 (m, 6H), 3.97 (s, 2H), 3.59 (t, J=6.0 Hz, 2H), 3.45 (t, J=6.8 Hz, 2H), 3.29 (s, 3H), 1.75-1.70 (m, 4H).

Example 4

(1) Preparation of 4-[N-(5,6-diphenylpyrazin-2-yl)-N-isopropylamino]-1-butanol 35.8 g (0.1 mol) of 2-iodo-5,6-diphenylpyrazin and 105 g (0.8 mol) of 4-isopropylamino-1-butanol was added into a 500 mL flask. Under the protection of nitrogen, the mixture was heated to 170° C. and reacted at this temperature for 4 hours, then cooled to 120° C. 80 g of 4-isopropylamino-1-butanol was recovered by vacuum distillation, the residue was cooled and samples were taken for testing, HPLC purity of the product was 96.2%, acetonitrile was added to recrystallize, and 31.8 g white solids of 4-[N-(5,6-diphenylpyrazin-2-yl)-N-isopropylamino]-1-butanol was obtained, the molar yield was 88%, HPLC purity was 99.3%, free of impurity S.

$^1$H-NMR data: $^1$H-NMR (400 MHz, CDCl$_3$) δ 8.02 (s, 1H), 7.46 (d, 2H, J=7.6 Hz), 7.36 (d, 2H, J=7.2 Hz), 7.28-7.22 (m, 6H), 4.80-4.78 (m, 1H), 3.71 (t, 2H, J=6.4 Hz), 3.45 (t, 2H, J=7.6 Hz), 1.77-1.74 (m, 2H), 1.66-1.64 (m, 2H), 1.29 (d, 6H, J=6.8 Hz).

(2) Preparation of 2-{4-[N-(5,6-diphenylpyrazin-2-yl)-N-isopropylamino]butyloxy}tert-butyl acetate 18.5 g (0.05 mol) of 4-[N-(5,6-diphenylpyrazin-2-yl)-N-isopropylamino]-1-butanol, 200 mL of toluene, 40 g of 45% aqueous solution of potassium hydroxide and 2 g of tetrabutylammonium bromide were added into a 500 mL flask and cooled to 5° C. by ice water, 30 g (0.15 mol) of tert-butyl bromoacetate was added dropwise, then reacted at this temperature for 4 hours until HPLC analysis showed the raw materials were reacted completely.

The mixture was placed to separate into layers, the aqueous phase was extracted once with 100 mL of toluene, the combined organic phase was washed with water and dried with anhydrous sodium sulfate, concentrated, toluene was recovered, and 23.5 g of 2-{4-[N-(5,6-diphenylpyrazin-2-yl)-N-isopropylamino]butyloxy}tert-butyl acetate was obtained, the molar yield was 99%, HPLC purity was 95%.

(3) Preparation of 2-{4-[N-(5,6-diphenylpyrazin-2-yl)-N-isopropylamino] butyloxy} acetic acid 23.8 g of 2-{4-[N-(5,6-diphenylpyrazin-2-yl)-N-isopropylamino]butyloxy}tert-butyl acetate (obtained by the previous reaction) and 115 mL of anhydrous ethanol were added into a 500 mL flask and cooled to 10° C., 20 g of 50% aqueous solution of sodium hydroxide was added dropwise, then reacted at this temperature for 2 hours until the reaction was completed.

The reaction solution was adjusted to pH 1-2 with concentrated hydrochloric acid and extracted with ethyl acetate, the organic phase was concentrated, the obtained crude product was recrystallized by 100 mL of isopropanol, and 17.9 g of 2-{4-[N-(5,6-diphenylpyrazin-2-yl)-N-isopropylamino] butyloxy} acetic acid was obtained, the molar yield was 85%, HPLC purity was 99.3%.

$^1$H-NMR data: $^1$H-NMR (400 MHz, CDCl$_3$) δ 8.03 (s, 1H), 7.35 (d, 2H, J=7.2 Hz), 7.24 (d, 2H, J=7.2 Hz), 7.17-7.15 (m, 6H), 4.80-4.77 (m, 1H), 4.0 (s, 2H), 3.56 (t, 2H, J=6.0 Hz), 3.38 (t, 2H, J=6.4 Hz), 1.71-1.66 (m, 4H), 1.20 (d, 6H, J=6.8 Hz).

(4) Preparation of NS-304

8.4 g (0.02 mol) of 2-{4-[N-(5,6-diphenylpyrazin-2-yl)-N-isopropylamino]butyloxy} acetic acid and 60 mL of dichloromethane were added into a 100 mL flask and cooled to 5° C., 3.8 g (0.03 mol) of oxalyl chloride was added dropwise, then reacted at room temperature for 2 hours, the solvent was concentrated to dryness, 50 mL of acetonitrile was added to dissolve, and the ×4 solution was obtained as a stand-by.

2.85 g of methanesulfonamide, 20 mL of acetonitrile and 3 g of triethylamine were added into another flask and cooled to 10° C., the ×4 solution obtained above was added dropwise, then reacted at this temperature for 5 hours, until the reaction was completed.

The finished reaction solution was poured into 100 mL of ice water, the mixture was extracted with ethyl acetate, the solvent of the organic phase was concentrated to dry, the residue was recrystallized with ethanol, and 8.8 g off-white crystals of NS-304 was obtained, the molar yield was 88%, HPLC purity was 99.5%.

$^1$H-NMR data: $^1$H-NMR (400 MHz, CDCl$_3$) δ: 8.19 (s, 1H), 7.44 (m, 2H), 7.35 (m, 2H), 7.30-7.21 (m, 6H), 3.97 (s, 2H), 3.59 (t, J=6.0 Hz, 2H), 3.45 (t, J=6.8 Hz, 2H), 3.29 (s, 3H), 1.75-1.70 (m, 4H).

Comparative Example 1: (Reference to the Preparation Method of Patent Document CN102459198A)

(1) Preparation of 4-[N-(5,6-diphenylpyrazin-2-yl)-N-isopropylamino]-1-butanol 35.8 g (0.1 mol) of 2-iodo-5,6-diphenylpyrazin, 180 mL of dimethylsulfoxide, 39.4 g (0.3 mol) of 4-isopropylamino-1-butanol and 25 g (0.3 mol) of sodium bicarbonate were added into a 500 mL flask. Under the protection of nitrogen, the mixture was heated to 180° C. and reacted at this temperature for 7 hours, cooled, samples were taken for testing, HPLC purity of the product was 76.0% and the content of impurity S was 13%. The reaction solution was poured into 1 L of ice water, the mixture was extracted with ethyl acetate 200 mL×3, the organic phases were combined and the solvent was concentrated to dryness, then the residue was purified by column chromatography, and 22.7 g of 4-[N-(5,6-diphenylpyrazin-2-yl)-N-isopropylamino]-1-butanol was obtained, HPLC purity was 97.6%, the molar yield was 63%.

$^1$H-NMR data: $^1$H-NMR (400 MHz, CDCl$_3$) δ 8.02 (s, 1H), 7.46 (d, 2H, J=7.6 Hz), 7.36 (d, 2H, J=7.2 Hz), 7.28-7.22 (m, 6H), 4.80-4.78 (m, 1H), 3.71 (t, 2H, J=6.4 Hz), 3.45 (t, 2H, J=7.6 Hz), 1.77-1.74 (m, 2H), 1.66-1.64 (m, 2H), 1.29 (d, 6H, J=6.8 Hz).

Comparative Example 2: (Reference to the Preparation Method of Patent Document WO2002088084A1)

(1) Preparation of 4-[N-(5,6-diphenylpyrazin-2-yl)-N-isopropylamino]-1-butanol 30 g of 2-chloro-5,6-diphenylpyrazin and 131.22 g (0.3 mol) of 4-isopropylamino-1-butanol were added into a 500 mL flask, the mixture was heated to 190° C. and reacted at this temperature for 10 hours, cooled, samples were taken for testing, HPLC purity of the product was 63.5%. The reaction solution was poured into 1 L of ice water, the mixture was extracted with ether 200 mL×3, the organic phases were combined and the solvent was concentrated to dryness, then the residue was purified by column chromatography, and 22.96 g of 4-[N-(5,6-diphenylpyrazin-2-yl)-N-isopropylamino]-1-butanol was obtained, HPLC purity was 97.2%, the molar yield was 56%.

¹H-NMR data: ¹H-NMR (400 MHz, CDCl₃) δ 8.02 (s, 1H), 7.46 (d, 2H, J=7.6 Hz), 7.36 (d, 2H, J=7.2 Hz), 7.28-7.22 (m, 6H), 4.80-4.78 (m, 1H), 3.71 (t, 2H, J=6.4 Hz), 3.45 (t, 2H, J=7.6 Hz), 1.77-1.74 (m, 2H), 1.66-1.64 (m, 2H), 1.29 (d, 6H, J=6.8 Hz).

(2) Preparation of 2-{4-[N-(5,6-diphenylpyrazin-2-yl)-N-isopropylamino]butyloxy}tert-butyl acetate 22.84 g of 4-[N-(5,6-diphenylpyrazin-2-yl)-N-isopropylamino]-1-butanol, 160 mL of toluene, 160 mL of 40% aqueous solution of potassium hydroxide and 10.73 g of tetrabutyl ammonium bisulfate were added into a 500 mL flask and cooled to 5° C. by ice water, 10.73 g of tert-butyl bromoacetate was added dropwise and reacted at this temperature for 45 minutes, then reacted at room temperature for 1 hour. After diluted with water, extracted with ether and purified by silica gel column chromatography, 21.7 g of 2-{4-[N-(5,6-diphenylpyrazin-2-yl)-N-isopropylamino]butyloxy}tert-butyl acetate was obtained, the molar yield was 72.3%, HPLC purity was 97%.

(3) Preparation of 2-{4-[N-(5,6-diphenylpyrazin-2-yl)-N-isopropylamino] butyloxy} acetic acid 21.7 g of 2-{4-[N-(5,6-diphenylpyrazin-2-yl)-N-isopropylamino]butyloxy}tert-butyl acetate, 200 mL of methanol and 60 mL of 1N aqueous solution of sodium hydroxide were added into a 500 mL flask, the mixture was refluxed to react for 2 hours, the solvent was concentrated to dryness, the residue was dissolved in water, impurities were extracted with ether, the aqueous phase was neutralized with 60 mL of 1N hydrochloric acid and extracted with ethyl acetate, the obtained solids were washed with isopropyl ether and dried, 18.82 g of 2-{4-[N-(5,6-diphenylpyrazin-2-yl)-N-isopropylamino] butyloxy} acetic acid was obtained, the molar yield was 85%, HPLC purity was 97.3%.

¹H-NMR data: ¹H-NMR (400 MHz, CDCl₃) δ 8.03 (s, 1H), 7.35 (d, 2H, J=7.2 Hz), 7.24 (d, 2H, J=7.2 Hz), 7.17-7.15 (m, 6H), 4.80-4.77 (m, 1H), 4.0 (s, 2H), 3.56 (t, 2H, J=6.0 Hz), 3.38 (t, 2H, J=6.4 Hz), 1.71-1.66 (m, 4H), 1.20 (d, 6H, J=6.8 Hz).

(4) Preparation of NS-304

Under the protection of nitrogen, 300 mg of 2-{4-[N-(5,6-diphenylpyrazin-2-yl)-N-isopropylamino] butyloxy} acetic acid, 5 mL of tetrahydrofuran and 128 mg of carbonyldiimidazole (CDI) were added into a 25 mL flask, the mixture was stirred at room temperature for 30 minutes, refluxed for 30 minutes, then cooled to room temperature, 69 mg of methanesulfonamide was added and stirred for 10 minutes, then 0.11 mL of 1,8-Diazabicyclo[5.4.0]undec-7-ene (DBU) was added and stirred overnight at room temperature, the reaction solution was diluted with water and extracted with ether, the organic phase was dried with magnesium sulfate, the solvent was concentrated to dryness, then the residue was purified by column chromatography, and 272 mg off-white crystals of NS-304 was obtained, the molar yield was 76%, HPLC purity was 98.1%.

¹H-NMR data: ¹H-NMR (400 MHz, CDCl₃) δ: 8.19 (s, 1H), 7.44 (m, 2H), 7.35 (m, 2H), 7.30-7.21 (m, 6H), 3.97 (s, 2H), 3.59 (t, J=6.0 Hz, 2H), 3.45 (t, J=6.8 Hz, 2H), 3.29 (s, 3H), 1.75-1.70 (m, 4H).

What is claimed:

1. A method for preparing 4-[N-(5,6-diphenylpyrazin-2-yl)-N-isopropylamino]-1-butanol of the following formula:

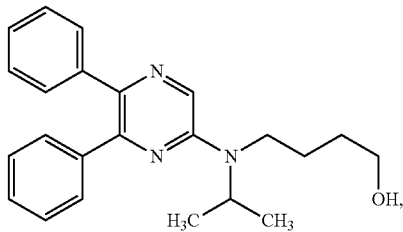 [SMILES: CC(C)N(CCCCO)c1cnc(-c2ccccc2)c(-c2ccccc2)n1]

the method comprising:
reacting 2-iodo-5,6-diphenylpyrazine of the formula:

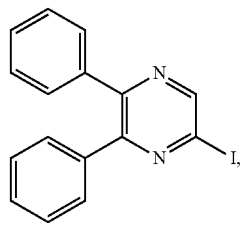 [SMILES: Ic1cnc(-c2ccccc2)c(-c2ccccc2)n1]

with 4-(N-isopropylamino)-1-butanol of the formula:

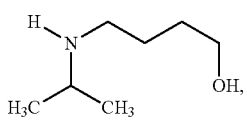

in the absence of solvents and acid-binding agents, to obtain 4-[N-(5,6-diphenylpyrazin-2-yl)-N-isopropylamino]-1-butanol of the formula above.

2. The method according to claim 1, wherein the molar ratio of 4-(N-isopropylamino)-1-butanol to 2-iodo-5,6-diphenylpyrazine is from 1:1 to 20:1.

3. The method according to claim 2, wherein the molar ratio of 4-(N-isopropylamino)-1-butanol to 2-iodo-5,6-diphenylpyrazine is from 5:1 to 15:1.

4. The method according to claim 1, wherein the reaction temperature is from 130° C. to 200° C. and the reaction time is from 2 hours to 10 hours.

5. The method according to claim 4, wherein the reaction temperature is from 150° C. to 180° C. and the reaction time is from 3 hours to 6 hours.

* * * * *